(12) United States Patent
Springmeyer (10) Patent No.: US 8,079,368 B2
(45) Date of Patent: *Dec. 20, 2011

(54) BRONCHOSCOPIC LUNG VOLUME REDUCTION METHOD

(75) Inventor: Steven C. Springmeyer, Bellevue, WA (US)

(73) Assignee: Spiration, Inc., Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/721,426

(22) Filed: Mar. 10, 2010

(65) Prior Publication Data

US 2010/0256714 A1    Oct. 7, 2010

Related U.S. Application Data

(63) Continuation of application No. 11/417,944, filed on May 3, 2006, now abandoned, which is a continuation of application No. 10/409,785, filed on Apr. 8, 2003, now Pat. No. 7,100,616.

(51) Int. Cl.
*A61B 19/00* (2006.01)
*A61M 16/00* (2006.01)
*A61M 37/00* (2006.01)
*A61M 1/00* (2006.01)
*A61M 31/00* (2006.01)
*A62B 9/02* (2006.01)
*A62B 9/06* (2006.01)
*A61F 7/00* (2006.01)

(52) U.S. Cl. .............. 128/898; 128/207.15; 128/207.16; 604/26; 604/27; 604/28; 604/514; 604/48; 604/93.01; 607/105

(58) Field of Classification Search .......... 128/207.15–207.16, 898
See application file for complete search history.

(56) References Cited

U.S. PATENT DOCUMENTS

| 2,832,078 A | 4/1958 | Williams |
| 2,981,254 A | 4/1961 | Vanderbilt |
| 3,320,972 A | 5/1967 | High et al. |
| 3,370,305 A | 2/1968 | Goott et al. |

(Continued)

FOREIGN PATENT DOCUMENTS

AU    2002239759    5/2002

(Continued)

OTHER PUBLICATIONS

U.S. Appl. No. 10/409,785, including its prosecution history, and the Office Actions therein.

(Continued)

*Primary Examiner* — David Isabella
*Assistant Examiner* — Andrew Iwamaye
(74) *Attorney, Agent, or Firm* — Knobbe, Martens, Olson & Bear LLP (57) ABSTRACT

A method of minimally invasively reducing a volume of a hyper-inflated target section of diseased lung comprising the steps of introducing a bronchoscope into a patient's airway to a position adjacent the target section and equilibrating air within the target section with atmospheric air to at least partially deflate the target lung section; injecting an inflammation-causing substance into the target section to precipitate adhesion of the walls within the target lung section, preventing substantial re-inflation of the target section by occluding an airway upstream of the target section for a period of time, and removing the airway occlusion after the target section has substantially permanently been reduced in volume. The injected substance can be autologous blood or a constituent thereof.

19 Claims, 5 Drawing Sheets

U.S. PATENT DOCUMENTS

| | | |
|---|---|---|
| 3,445,916 A | 5/1969 | Schulte |
| 3,472,230 A | 10/1969 | Forgarty |
| 3,540,431 A | 11/1970 | Modin-Uddin |
| 3,617,060 A | 11/1971 | Iezzi |
| 3,657,744 A | 4/1972 | Ersek |
| 3,671,979 A | 6/1972 | Moulopoulos |
| 3,683,913 A | 8/1972 | Kurtz et al. |
| 3,757,783 A | 9/1973 | Alley |
| 3,760,808 A | 9/1973 | Bleuer |
| 3,788,327 A | 1/1974 | Donowitz et al. |
| 3,874,388 A | 4/1975 | King et al. |
| 4,014,318 A | 3/1977 | Dockum et al. |
| 4,040,428 A | 8/1977 | Clifford |
| 4,056,854 A | 11/1977 | Boretos et al. |
| 4,084,268 A | 4/1978 | Ionescu et al. |
| 4,086,665 A | 5/1978 | Poirier |
| 4,212,463 A | 7/1980 | Repski et al. |
| 4,218,782 A | 8/1980 | Rygg |
| 4,222,126 A | 9/1980 | Boretos et al. |
| 4,250,873 A | 2/1981 | Bonnet |
| 4,301,810 A | 11/1981 | Belman |
| 4,302,854 A | 12/1981 | Runge |
| 4,339,831 A | 7/1982 | Johnson |
| RE31,040 E | 9/1982 | Possis |
| 4,403,616 A | 9/1983 | King |
| 4,456,016 A | 6/1984 | Nowacki et al. |
| 4,512,338 A | 4/1985 | Balko et al. |
| 4,533,137 A | 8/1985 | Sonne |
| 4,569,674 A | 2/1986 | Phillips et al. |
| 4,582,058 A | 4/1986 | Depel et al. |
| 4,592,741 A | 6/1986 | Vincent |
| 4,601,465 A | 7/1986 | Roy |
| 4,610,256 A | 9/1986 | Wallace |
| 4,619,246 A | 10/1986 | Molgaard-Nielsen et al. |
| 4,654,027 A | 3/1987 | Dragan et al. |
| 4,654,029 A | 3/1987 | D'Antonio |
| 4,681,110 A | 7/1987 | Wiktor |
| 4,684,363 A | 8/1987 | Ari et al. |
| 4,685,908 A | 8/1987 | Kurtz |
| 4,710,192 A | 12/1987 | Liotta et al. |
| 4,727,873 A | 3/1988 | Mobin-Uddin |
| 4,732,152 A | 3/1988 | Wallsten et al. |
| 4,745,925 A | 5/1988 | Dietz |
| 4,759,758 A | 7/1988 | Gabbay |
| 4,795,449 A | 1/1989 | Schneider et al. |
| 4,808,183 A | 2/1989 | Panje |
| 4,819,664 A | 4/1989 | Nazari |
| 4,822,354 A | 4/1989 | Elosegui |
| 4,830,003 A | 5/1989 | Wolff et al. |
| 4,832,680 A | 5/1989 | Haber et al. |
| 4,846,836 A | 7/1989 | Reich |
| 4,850,999 A | 7/1989 | Planck |
| 4,852,568 A | 8/1989 | Kensey |
| 4,877,025 A | 10/1989 | Hanson |
| 4,908,028 A | 3/1990 | Colon et al. |
| 4,934,999 A | 6/1990 | Bader |
| 4,936,823 A | 6/1990 | Colvin et al. |
| 4,968,294 A | 11/1990 | Salama |
| 4,973,047 A | 11/1990 | Norell |
| 4,979,505 A | 12/1990 | Cox |
| 4,984,581 A | 1/1991 | Stice |
| 5,033,312 A | 7/1991 | Stupecky |
| 5,038,621 A | 8/1991 | Stupecky |
| 5,059,208 A | 10/1991 | Coe et al. |
| 5,061,274 A | 10/1991 | Kensey |
| 5,078,739 A | 1/1992 | Martin |
| 5,092,781 A | 3/1992 | Casciotti et al. |
| 5,116,360 A | 5/1992 | Pinchuk et al. |
| 5,116,564 A | 5/1992 | Jansen et al. |
| 5,123,919 A | 6/1992 | Sauter et al. |
| 5,135,488 A | 8/1992 | Foote et al. |
| 5,151,105 A | 9/1992 | Kwan-Gett |
| 5,158,548 A | 10/1992 | Lau et al. |
| 5,161,524 A | 11/1992 | Evans |
| 5,171,299 A | 12/1992 | Heitzmann et al. |
| 5,197,980 A | 3/1993 | Gorshkov et al. |
| 5,255,687 A | 10/1993 | McKenna |
| 5,275,169 A | 1/1994 | Afromowitz et al. |
| 5,283,063 A | 2/1994 | Freeman |
| 5,300,050 A | 4/1994 | Everett, Jr. et al. |
| 5,304,199 A | 4/1994 | Myers |
| 5,306,234 A | 4/1994 | Johnson |
| 5,314,473 A | 5/1994 | Godin |
| 5,339,805 A | 8/1994 | Parker |
| 5,342,298 A | 8/1994 | Michaels |
| 5,352,240 A | 10/1994 | Ross |
| 5,353,470 A | 10/1994 | Bartlett |
| 5,358,518 A | 10/1994 | Camilli |
| 5,366,478 A | 11/1994 | Brinkerhoff et al. |
| 5,370,657 A | 12/1994 | Irie |
| 5,382,261 A | 1/1995 | Palmaz |
| 5,383,470 A | 1/1995 | Kolby |
| 5,391,205 A | 2/1995 | Knight |
| 5,392,775 A | 2/1995 | Adkins, Jr. et al. |
| 5,398,844 A | 3/1995 | Zaslavsky |
| 5,409,019 A | 4/1995 | Wilk |
| 5,409,444 A | 4/1995 | Kensey et al. |
| 5,411,507 A | 5/1995 | Heckele |
| 5,411,552 A | 5/1995 | Anderson et al. |
| 5,413,599 A | 5/1995 | Imachi et al. |
| 5,415,660 A | 5/1995 | Campbell et al. |
| 5,417,226 A | 5/1995 | Juma |
| 5,421,325 A | 6/1995 | Cinberg et al. |
| 5,445,626 A | 8/1995 | Gigante |
| 5,453,090 A | 9/1995 | Martenez et al. |
| 5,459,544 A | 10/1995 | Emura |
| 5,484,444 A | 1/1996 | Braunschweiler et al. |
| 5,486,154 A | 1/1996 | Kelleher |
| 5,499,995 A | 3/1996 | Teirstein |
| 5,500,014 A | 3/1996 | Quijano et al. |
| RE35,225 E | 4/1996 | Herweck et al. |
| 5,507,754 A | 4/1996 | Green et al. |
| 5,507,797 A | 4/1996 | Suzuki |
| 5,509,900 A | 4/1996 | Kirkman |
| 5,514,153 A | 5/1996 | Bonutti et al. |
| 5,549,626 A | 8/1996 | Miller et al. |
| 5,549,628 A | 8/1996 | Cooper et al. |
| 5,562,608 A | 10/1996 | Sekins et al. |
| 5,562,641 A | 10/1996 | Flomenblit et al. |
| 5,562,728 A | 10/1996 | Lazarus et al. |
| 5,603,698 A | 2/1997 | Roberts et al. |
| 5,607,469 A | 3/1997 | Frey |
| 5,645,565 A | 7/1997 | Rudd et al. |
| 5,647,857 A | 7/1997 | Andersen et al. |
| 5,660,175 A | 8/1997 | Dayal |
| 5,662,713 A | 9/1997 | Anderson et al. |
| 5,669,933 A | 9/1997 | Simon et al. |
| 5,676,671 A | 10/1997 | Inoue |
| 5,683,451 A | 11/1997 | Lenker et al. |
| 5,690,644 A | 11/1997 | Yurek et al. |
| 5,693,089 A | 12/1997 | Inoue |
| 5,697,968 A | 12/1997 | Rogers et al. |
| 5,702,343 A | 12/1997 | Alferness |
| 5,702,409 A | 12/1997 | Rayburn et al. |
| 5,725,519 A | 3/1998 | Penner et al. |
| 5,752,522 A | 5/1998 | Murphy |
| 5,752,965 A | 5/1998 | Francis et al. |
| 5,755,770 A | 5/1998 | Ravenscroft |
| 5,763,979 A | 6/1998 | Mukherjee et al. |
| 5,782,896 A | 7/1998 | Chen et al. |
| 5,797,920 A | 8/1998 | Kim |
| 5,797,960 A | 8/1998 | Stevens et al. |
| 5,800,339 A | 9/1998 | Salama |
| 5,803,078 A | 9/1998 | Brauner |
| 5,810,837 A | 9/1998 | Hofmann et al. |
| 5,817,101 A | 10/1998 | Fiedler |
| 2,479,805 A | 11/1998 | Sabaratnam |
| 5,830,217 A | 11/1998 | Ryan |
| 5,833,694 A | 11/1998 | Poncet |
| 5,840,081 A | 11/1998 | Anderson et al. |
| 5,851,232 A | 12/1998 | Lois |
| 5,855,587 A | 1/1999 | Hyon et al. |
| 5,855,597 A | 1/1999 | Jayaraman |
| 5,855,601 A | 1/1999 | Bessler et al. |
| 5,876,434 A | 3/1999 | Flomenblit et al. |
| 5,876,445 A | 3/1999 | Andersen et al. |
| 5,911,756 A | 6/1999 | Debry |

| | | | | | | |
|---|---|---|---|---|---|---|
| 5,925,063 A | 7/1999 | Khosravi | 6,425,916 B1 | 7/2002 | Garrison et al. | |
| 5,944,738 A | 8/1999 | Amplatz et al. | 6,428,561 B1 | 8/2002 | Johansson-Ruden et al. | |
| 5,947,997 A | 9/1999 | Pavcnik et al. | 6,439,233 B1 | 8/2002 | Geertsema | |
| 5,954,636 A | 9/1999 | Schwartz et al. | 6,440,164 B1 | 8/2002 | DiMatteo et al. | |
| 5,954,766 A | 9/1999 | Zadno-Azizi et al. | 6,447,530 B1 | 9/2002 | Ostrovsky et al. | |
| 5,957,949 A | 9/1999 | Leonhardt et al. | 6,454,754 B1 | 9/2002 | Frank | |
| 5,957,978 A | 9/1999 | Blom | 6,458,076 B1 | 10/2002 | Pruitt | |
| 5,972,009 A | 10/1999 | Fortier et al. | 6,458,153 B1 | 10/2002 | Bailey et al. | |
| 5,976,158 A | 11/1999 | Adams et al. | 6,471,718 B1 | 10/2002 | Staehle et al. | |
| 5,976,174 A | 11/1999 | Ruiz | 6,471,979 B2 | 10/2002 | New et al. | |
| 5,984,965 A | 11/1999 | Knapp et al. | 6,485,407 B2 | 11/2002 | Alferness et al. | |
| 5,989,234 A | 11/1999 | Valerio et al. | 6,488,673 B1 * | 12/2002 | Laufer et al. | 604/516 |
| 6,003,517 A | 12/1999 | Sheffield et al. | 6,491,706 B1 | 12/2002 | Alferness et al. | |
| 6,007,575 A | 12/1999 | Samuels | 6,493,589 B1 * | 12/2002 | Medhkour et al. | 607/99 |
| 6,009,614 A | 1/2000 | Morales | 6,503,272 B2 | 1/2003 | Duerig et al. | |
| 6,010,511 A | 1/2000 | Murphy | 6,510,846 B1 | 1/2003 | O'Rourke | |
| 6,010,525 A | 1/2000 | Bonutti et al. | 6,514,290 B1 | 2/2003 | Loomas | |
| 6,020,380 A | 2/2000 | Killian | 6,527,761 B1 * | 3/2003 | Soltesz et al. | 604/516 |
| 6,027,525 A | 2/2000 | Suh et al. | 6,540,782 B1 | 4/2003 | Snyders | |
| 6,045,560 A | 4/2000 | McKean et al. | 6,544,192 B2 | 4/2003 | Starr et al. | |
| 6,051,022 A | 4/2000 | Cai et al. | 6,544,291 B2 | 4/2003 | Taylor | |
| 6,068,635 A | 5/2000 | Gianotti | 6,558,429 B2 | 5/2003 | Taylor | |
| 6,068,638 A | 5/2000 | Makower | 6,568,387 B2 | 5/2003 | Davenport et al. | |
| 6,077,291 A | 6/2000 | Das | 6,569,166 B2 | 5/2003 | Gonzalez | |
| 6,079,413 A | 6/2000 | Baran | 6,585,639 B1 | 7/2003 | Kotmel et al. | |
| 6,083,141 A | 7/2000 | Hougen | 6,589,256 B2 | 7/2003 | Forber | |
| 6,083,255 A | 7/2000 | Laufer et al. | 6,592,594 B2 | 7/2003 | Rimbaugh et al. | |
| 6,096,027 A | 8/2000 | Layne | 6,599,311 B1 | 7/2003 | Biggs et al. | |
| 6,099,551 A | 8/2000 | Gabbay | 6,600,307 B2 | 7/2003 | Turski | |
| 6,123,663 A | 9/2000 | Rebuffat | 6,610,043 B1 | 8/2003 | Ingenito | |
| 6,132,458 A | 10/2000 | Staehle et al. | 6,629,951 B2 | 10/2003 | Laufer et al. | |
| 6,135,729 A | 10/2000 | Aber | 6,632,243 B1 | 10/2003 | Zadno-Azizi et al. | |
| 6,135,991 A | 10/2000 | Muni et al. | 6,634,363 B1 | 10/2003 | Danek et al. | |
| 6,141,855 A | 11/2000 | Morales | 6,638,285 B2 | 10/2003 | Gabbay | |
| 6,146,357 A | 11/2000 | Addis | 6,669,724 B2 | 12/2003 | Park et al. | |
| 6,149,664 A | 11/2000 | Kurz | 6,673,070 B2 | 1/2004 | Edwards et al. | |
| 6,162,245 A | 12/2000 | Jayaraman | 6,679,264 B1 | 1/2004 | Deem et al. | |
| 6,165,179 A | 12/2000 | Cathcart et al. | 6,682,250 B2 | 1/2004 | Banks | |
| 6,168,614 B1 | 1/2001 | Andersen et al. | 6,682,520 B2 | 1/2004 | Ingenito | |
| 6,168,617 B1 | 1/2001 | Blaeser et al. | 6,694,979 B2 | 2/2004 | Deem et al. | |
| 6,174,307 B1 | 1/2001 | Daniel et al. | 6,709,401 B2 | 3/2004 | Perkins et al. | |
| 6,174,323 B1 | 1/2001 | Biggs | 6,712,812 B2 | 3/2004 | Roschak et al. | |
| 6,183,520 B1 | 2/2001 | Pintauro et al. | 6,716,208 B2 | 4/2004 | Humes | |
| 6,193,748 B1 | 2/2001 | Thompson et al. | 6,722,360 B2 | 4/2004 | Doshi | |
| 6,200,333 B1 | 3/2001 | Laufer | 6,743,259 B2 | 6/2004 | Ginn | |
| 6,203,551 B1 | 3/2001 | Wu | 6,746,686 B2 | 6/2004 | Hughes et al. | |
| 6,206,918 B1 | 3/2001 | Campbell et al. | 6,749,606 B2 | 6/2004 | Keast et al. | |
| 6,210,338 B1 | 4/2001 | Afremov et al. | 6,840,952 B2 | 1/2005 | Saker et al. | |
| 6,231,587 B1 | 5/2001 | Makower | 6,849,049 B2 | 2/2005 | Starr et al. | |
| 6,231,589 B1 | 5/2001 | Wessman et al. | 6,849,084 B2 | 2/2005 | Rabkin et al. | |
| 6,234,996 B1 | 5/2001 | Bagaoisan et al. | 6,860,847 B2 | 3/2005 | Alferness et al. | |
| 6,238,334 B1 | 5/2001 | Easterbrook, III et al. | 6,887,256 B2 | 5/2005 | Gilson | |
| 6,240,615 B1 | 6/2001 | Kimes et al. | 6,904,909 B2 | 6/2005 | Andreas et al. | |
| 6,241,654 B1 | 6/2001 | Alferness | 6,929,637 B2 | 8/2005 | Gonzalez et al. | |
| 6,241,678 B1 | 6/2001 | Afremov et al. | 6,941,950 B2 | 9/2005 | Wilson et al. | |
| 6,241,758 B1 | 6/2001 | Cox | 6,951,571 B1 | 10/2005 | Srivastava | |
| 6,242,472 B1 | 6/2001 | Sekins et al. | 6,958,076 B2 | 10/2005 | Acosta et al. | |
| 6,245,102 B1 | 6/2001 | Jayaraman | 6,989,027 B2 | 1/2006 | Allen et al. | |
| 6,258,100 B1 | 7/2001 | Alferness et al. | 6,997,951 B2 | 2/2006 | Solem et al. | |
| 6,264,700 B1 | 7/2001 | Kilcoyne et al. | 7,011,094 B2 | 3/2006 | Rapacki et al. | |
| 6,267,775 B1 | 7/2001 | Clerc et al. | 7,086,398 B2 * | 8/2006 | Tanaka | 128/200.26 |
| 6,270,527 B1 | 8/2001 | Campbell et al. | 7,100,616 B2 * | 9/2006 | Springmeyer | 128/898 |
| 6,287,290 B1 | 9/2001 | Perkins et al. | 7,141,046 B2 | 11/2006 | Perkins et al. | |
| 6,287,334 B1 | 9/2001 | Moll et al. | 7,175,644 B2 | 2/2007 | Cooper et al. | |
| 6,293,951 B1 | 9/2001 | Alferness et al. | 7,207,946 B2 | 4/2007 | Sirokman | |
| 6,299,604 B1 | 10/2001 | Ragheb et al. | 7,252,086 B2 | 8/2007 | Tanaka | |
| 6,302,893 B1 | 10/2001 | Limon et al. | 7,278,430 B2 | 10/2007 | Kumar | |
| 6,312,407 B1 | 11/2001 | Zadno-Azizi et al. | 7,357,795 B2 | 4/2008 | Kaji et al. | |
| 6,325,777 B1 | 12/2001 | Zadno-Azizi et al. | 7,412,977 B2 | 8/2008 | Fields et al. | |
| 6,325,778 B1 | 12/2001 | Zadno-Azizi et al. | 7,422,584 B2 * | 9/2008 | Loomas et al. | 606/32 |
| 6,327,505 B1 * | 12/2001 | Medhkour et al. ............ 607/99 | 7,434,578 B2 | 10/2008 | Dillard et al. | |
| 6,327,772 B1 | 12/2001 | Zadno-Azizi et al. | 7,530,995 B2 | 5/2009 | Quijano et al. | |
| 6,328,689 B1 | 12/2001 | Gonzalez et al. | 7,533,671 B2 | 5/2009 | Gonzalez et al. | |
| 6,338,728 B1 | 1/2002 | Valerio et al. | 7,757,692 B2 | 7/2010 | Alferness et al. | |
| 6,350,278 B1 | 2/2002 | Lenker et al. | 7,798,974 B2 | 9/2010 | Sirokman | |
| 6,355,014 B1 | 3/2002 | Zadno-Azizi et al. | 7,842,061 B2 | 11/2010 | Dillard et al. | |
| 6,398,775 B1 | 6/2002 | Perkins et al. | 7,875,048 B2 | 1/2011 | Dillard et al. | |
| 6,402,754 B1 | 6/2002 | Gonzalez | 7,913,698 B2 * | 3/2011 | Barry et al. | 128/898 |
| 6,416,554 B1 | 7/2002 | Alferness et al. | 2001/0010017 A1 | 7/2001 | Letac et al. | |

| | | | | | | |
|---|---|---|---|---|---|---|
| 2001/0025132 A1 | 9/2001 | Alferness et al. | | CN | 101868199 | 10/2010 |
| 2001/0037808 A1 | 11/2001 | Deem et al. | | DE | 100 04 979 | 8/2000 |
| 2001/0041906 A1 | 11/2001 | Gonzalez | | EP | 0 665 029 | 8/1995 |
| 2001/0051799 A1 | 12/2001 | Ingenito | | EP | 0 743 071 | 11/1996 |
| 2001/0052344 A1 | 12/2001 | Doshi | | EP | 1 151 729 | 7/2001 |
| 2001/0056274 A1 | 12/2001 | Perkins et al. | | EP | 1 157 663 | 11/2001 |
| 2002/0007831 A1 | 1/2002 | Davenport et al. | | EP | 1 206 276 | 5/2002 |
| 2002/0062120 A1 | 5/2002 | Perkins et al. | | EP | 1 198 269 | 10/2009 |
| 2002/0077564 A1 | 6/2002 | Campbell et al. | | GB | 2 082 071 | 3/1982 |
| 2002/0077593 A1 | 6/2002 | Perkins et al. | | GB | 2 324 729 | 11/1998 |
| 2002/0077696 A1 | 6/2002 | Zadno-Azizi et al. | | GB | 2 348 138 | 9/2000 |
| 2002/0087153 A1 | 7/2002 | Roschak et al. | | JP | 58-163332 | 9/1983 |
| 2002/0091411 A1 | 7/2002 | Saker et al. | | JP | 60-10740 | 1/1994 |
| 2002/0095209 A1 | 7/2002 | Zadno-Azizi et al. | | JP | 2003-503162 | 1/2003 |
| 2002/0111619 A1 | 8/2002 | Keast et al. | | JP | 2004-535887 | 12/2004 |
| 2002/0111620 A1 | 8/2002 | Cooper et al. | | JP | 2005-527297 | 9/2005 |
| 2002/0112729 A1 | 8/2002 | Devore et al. | | JP | 3742010 | 11/2005 |
| 2002/0123749 A1 | 9/2002 | Jain | | JP | 4387803 B2 | 10/2009 |
| 2002/0138135 A1 | 9/2002 | Duerig et al. | | RU | 2140211 | 10/1999 |
| 2002/0147462 A1 | 10/2002 | Mair et al. | | SU | 852321 | 8/1981 |
| 2003/0018327 A1 | 1/2003 | Truckai et al. | | SU | 1371700 | 2/1988 |
| 2003/0018344 A1 | 1/2003 | Kaji et al. | | SU | 1593651 | 9/1990 |
| 2003/0024527 A1 | 2/2003 | Ginn | | WO | WO 88/09683 | 12/1988 |
| 2003/0050648 A1 | 3/2003 | Alferness et al. | | WO | WO 94/26175 | 11/1994 |
| 2003/0051733 A1 | 3/2003 | Kotmel et al. | | WO | WO 95/32018 | 11/1995 |
| 2003/0055331 A1 | 3/2003 | Kotmel et al. | | WO | WO 96/34582 | 11/1996 |
| 2003/0070682 A1* | 4/2003 | Wilson et al. ............ 128/207.16 | | WO | WO 97/09932 | 3/1997 |
| 2003/0083671 A1 | 5/2003 | Rimbaugh et al. | | WO | WO 97/13471 | 4/1997 |
| 2003/0109869 A1* | 6/2003 | Shadduck ........................ 606/41 | | WO | WO 97/27893 | 8/1997 |
| 2003/0125763 A1 | 7/2003 | McInnes | | WO | WO 97/42871 | 11/1997 |
| 2003/0127090 A1 | 7/2003 | Gifford et al. | | WO | WO 97/44085 | 11/1997 |
| 2003/0154988 A1 | 8/2003 | DeVore | | WO | WO 98/00840 | 1/1998 |
| 2003/0158515 A1 | 8/2003 | Gonzalez et al. | | WO | WO 98/01084 | 1/1998 |
| 2003/0180922 A1 | 9/2003 | Eaton et al. | | WO | WO 98/19633 | 5/1998 |
| 2003/0181922 A1 | 9/2003 | Alferness | | WO | WO 98/39047 | 9/1998 |
| 2003/0183235 A1 | 10/2003 | Rimbaugh et al. | | WO | WO 98/44854 | 10/1998 |
| 2003/0195385 A1 | 10/2003 | De Vore | | WO | WO 98/48706 | 11/1998 |
| 2003/0212412 A1 | 11/2003 | Dillard et al. | | WO | WO 99/01076 | 1/1999 |
| 2003/0212452 A1 | 11/2003 | Zadno-Azizi et al. | | WO | WO 99/13801 | 3/1999 |
| 2003/0216769 A1 | 11/2003 | Dillard et al. | | WO | WO 99/26692 | 6/1999 |
| 2003/0225445 A1 | 12/2003 | Derus et al. | | WO | WO 99/32040 | 7/1999 |
| 2003/0228344 A1 | 12/2003 | Fields et al. | | WO | WO 99/42059 | 8/1999 |
| 2004/0024356 A1* | 2/2004 | Tanaka ........................ 604/104 | | WO | WO 99/42161 | 8/1999 |
| 2004/0039250 A1 | 2/2004 | Tholfsen et al. | | WO | WO 99/59503 | 11/1999 |
| 2004/0040555 A1* | 3/2004 | Tanaka ..................... 128/200.24 | | WO | WO 99/64109 | 12/1999 |
| 2004/0059263 A1 | 3/2004 | DeVore | | WO | WO 00/18329 | 4/2000 |
| 2004/0143283 A1 | 7/2004 | McGill et al. | | WO | WO 00/27292 A | 5/2000 |
| 2004/0206349 A1 | 10/2004 | Alferness et al. | | WO | WO 00/42950 | 7/2000 |
| 2004/0210248 A1 | 10/2004 | Gordon et al. | | WO | WO 00/51500 A | 9/2000 |
| 2004/0211412 A1 | 10/2004 | Alferness et al. | | WO | WO 00/51510 | 9/2000 |
| 2004/0211434 A1* | 10/2004 | Loomas et al. ................ 128/898 | | WO | WO 00/62699 | 10/2000 |
| 2004/0243140 A1 | 12/2004 | Alferness et al. | | WO | WO 00/78386 | 12/2000 |
| 2004/0244802 A1 | 12/2004 | Tanaka | | WO | WO 00/78407 | 12/2000 |
| 2005/0033310 A1 | 2/2005 | Alferness et al. | | WO | WO 01/02042 | 1/2001 |
| 2005/0033344 A1 | 2/2005 | Dillard et al. | | WO | WO 01/03641 | 1/2001 |
| 2005/0096721 A1 | 5/2005 | Mangin et al. | | WO | WO 01/03642 | 1/2001 |
| 2005/0137611 A1 | 6/2005 | Escudero et al. | | WO | WO 01/05334 | 1/2001 |
| 2005/0145253 A1 | 7/2005 | Wilson et al. | | WO | WO 01/10313 | 2/2001 |
| 2005/0166925 A1 | 8/2005 | Wilson et al. | | WO | WO 01/10314 | 2/2001 |
| 2005/0222580 A1 | 10/2005 | Gifford, III et al. | | WO | WO 01/12104 | 2/2001 |
| 2005/0267323 A1 | 12/2005 | Dorros et al. | | WO | WO 01/13839 | 3/2001 |
| 2006/0074382 A1 | 4/2006 | Gonzalez et al. | | WO | WO 01/13908 | 3/2001 |
| 2006/0235467 A1 | 10/2006 | DeVore | | WO | WO 01/28433 | 4/2001 |
| 2006/0270940 A1 | 11/2006 | Tsukashima et al. | | WO | WO 01/30266 A | 5/2001 |
| 2007/0221230 A1 | 9/2007 | Thompson et al. | | WO | WO 01/37897 | 5/2001 |
| 2007/0225747 A1 | 9/2007 | Perkins et al. | | WO | WO 01/45590 | 6/2001 |
| 2008/0015627 A1 | 1/2008 | DeVore | | WO | WO 01/52775 | 7/2001 |
| 2008/0132989 A1 | 6/2008 | Snow et al. | | WO | WO 01/54585 | 8/2001 |
| 2009/0099530 A1 | 4/2009 | Adams et al. | | WO | WO 01/54625 | 8/2001 |
| 2009/0182369 A1 | 7/2009 | Gonzalez | | WO | WO 01/54685 | 8/2001 |
| 2009/0292262 A1 | 11/2009 | Adams et al. | | WO | WO 01/66190 | 9/2001 |
| 2010/0256714 A1 | 10/2010 | Springmeyer | | WO | WO01/66190 | 9/2001 |
| 2010/0262071 A1 | 10/2010 | Kutsko et al. | | WO | WO 01/70114 | 9/2001 |
| | | | | WO | WO 01/74271 | 10/2001 |
| | FOREIGN PATENT DOCUMENTS | | | WO | WO 01/87170 | 11/2001 |
| CA | 2308186 | 5/1999 | | WO | WO 01/89366 | 11/2001 |
| CA | 2375752 | 1/2001 | | WO | WO 01/49213 | 12/2001 |
| CA | 2401331 | 3/2001 | | WO | WO 01/95786 | 12/2001 |
| CA | 2408923 | 11/2001 | | WO | WO 02/05884 | 1/2002 |

| | | |
|---|---|---|
| WO | WO 02/22072 | 3/2002 |
| WO | WO 02/32333 | 4/2002 |
| WO | WO 02/34322 | 5/2002 |
| WO | WO 02/38038 | 5/2002 |
| WO | WO 02/47575 | 6/2002 |
| WO | WO 02/056794 | 7/2002 |
| WO | WO 02/064045 | 8/2002 |
| WO | WO 02/064190 | 8/2002 |
| WO | WO 02/069823 | 9/2002 |
| WO | WO 02/094087 | 11/2002 |
| WO | WO 01/95786 | 12/2002 |
| WO | WO 03/022124 | 3/2003 |
| WO | WO 03/030975 | 4/2003 |
| WO | WO 03/099164 | 4/2003 |
| WO | WO 03/003946 | 5/2003 |
| WO | WO 03/034927 | 5/2003 |
| WO | WO 03/041779 | 5/2003 |
| WO | WO 03/047468 | 6/2003 |
| WO | WO 03/078579 | 9/2003 |
| WO | WO 03/088820 | 10/2003 |
| WO | WO 03/094996 | 11/2003 |
| WO | WO 2004/010845 | 2/2004 |
| WO | WO 2004/080347 | 9/2004 |
| WO | WO 2005/013835 | 2/2005 |
| WO | WO 2007/123690 | 11/2007 |
| WO | WO 2009/049261 | 4/2009 |
| WO | WO 2010/118056 | 10/2010 |

OTHER PUBLICATIONS

Article: Autocath® 100-Nonsurgical, Intraurethral Bladder Control Device for Incontinent and Retentive Women—Dr. Kulisz's Development. Dated Feb. 26, 2004.
Dillard et al., "Evaluation of a Novel Intra-bronchial Valve Device to Produce Lung Volume Reduction." Poster shown at conference in Jun. 2002.
EWS Endobronchial Watanabe Spigots. Novatech, edited Apr. 17. 2002.
Harris et al., The Experimental Production in Dogs of Emphysema with Associated Asthmatic Syndrome by Means of an Interatracheal Ball Valve: J. EXD Med 30:1919; 75-88 dated Apr. 8, 1919.
Horiuchi et al: Three Cases of Intractable Pneumothorax Treated Successfully by Bronchial Embolization . using Silicon; JJSB. 2001. pp. 25-30.
Inaspettato: Endoscopic Treatment of Bronchopleural Fistulas Using N-butyl-2-cyanoacrylate; Surg.ical Laparoscopv & Endoscopy; vol. 4 No. 1. pp. 62-64. 1994.
Jones et al: Closure of a Benign Brancho-Oesophageal Fistula by Endoscopic Injection of Bovine Collagen. Cvanocrvlate Glue and Gelfoam; 1996. pp. 53-55 Aust. N.Z. J. Suro.
Lewis et al., "Pulmonary Interstitial Emphysema: Selective Bronchial Occlusion with a Swan-Ganz Catheter." Archives of Disease in Childhood, 63:1988, 313-315.
Mathew et al. Selective Bronchial Obstruction for Treatment of Bullous Interstitial Emphysema: J. of Ped. 96:1980, 475-477.
Okada et al: Emergent Bronchofiberoptic Bronchial Occlusion for Intractable Pneumothorax with Severe Emphysema; The Japanese Journal of Thoracic and Cardiovascular Surgerv, 1998. pp. 1078-1081.
Puhakka et al., "Acute Bronchial Obstruction: An Experimental Rabbit Model Study." Int. J. of Pediatric OtorhinolarvnQoloQy. 18:1989,107-118.
Snider et al., "The Definition of Emphysema: Report of the National Heart Lung and Blood Institute, Division of Lung Diseases Workshop", Am. Rev. Resoir. Dis., 132:182-185,1985.
Watanabe et al: Bronchial Embolization Using Dental Impression Material in a Case of Pyelo-bronchial Fistula with Candida Funqemia; 1991. Journal of the Japan Society for Broncholoqv, pp. 607-610.
Andre A. Kulisz, Autocath 100 -Nonsurgical, Intraurethral Bladder Control Device for Urinary Incontinent and Urinary Retentive Women—Another Dr. Kulisz's Development, http://www.kulisz.com/autocath.htm, 2003, 3 pp.
Australian Office Action of Oct. 29, 2007, Application No. 2003219927.
Canadian Office Action dated Apr. 28, 2009 for Canadian Application No. 2,459,702.
Canadian Office Action dated Dec. 14, 2010 for Canadian Application No. 2,459,702.
Canadian Office Action dated Mar. 9, 2010 for Canadian Application No. 2,459,702.
Canadian Office Action dated Nov. 5, 2009, re Application No. 2,484,086 in 2 pgs.
Canadian Office Action of Apr. 28, 2009, Application No. 2,479,805.
Chest Drains, from webmaster@atroi.ed/cp., from website Mar. 21, 2002; pp. 1-3.
Chest Drains, from webmaster@surgical-tutor.org.uk; from Website on Mar. 21, 2002; pp. 1-3.
Chinese Office Action dated Jun. 4, 2010 re CN Application No. 200780019455.6.
EDO Certamics Products and Services, from webmaster@edocorp.com; from website on Mar. 21, 2002; pp. 1,2.
Ellis, James H., Balloon Catheter Occlusion of Bronchopleural Fistulae, May 7, 1981, AJR: 138, Jan. 1982, p. 157-159.
European Examination Report dated Apr. 14, 2010 for EP Application No. 03 71 0804 in 5 pgs.
European Office Action of Dec. 23, 2008, Application No. 03 716 212.0-1265.
European Office Action of Dec. 8, 2010, Application No. 09739872.1.
European Office Action of Jan. 8, 2009, Application No. 03 716212.0.
European Office Action of Jun. 17, 2009, Application No. 03 716 212.0-1265.
European Search Report in European Appln. No. 02759335.9, dated Jan. 31, 2007.
European Supplemental Search Report dated Nov. 9, 2009 for EP Application No. 03 71 0804 in 2 pgs.
European Supplemental Search Report in European Appln. No. 00969008.2, dated Feb. 26, 2004, 5 pp.
European Supplemental Search Report of Feb. 28, 2008, Application No. 03 716 212.0-1265.
Exploring Chest Drain Options; from webmaster google.com; RNWeb: Continuing Education; from website on Mar. 21, 2002; pp. 1-6.
Extended European Search Report for EP 08 0205468, dated Jul. 28, 2009.
International Report on Patentability dated Dec. 23, 2009 re PCT/US2008/079650.
International Search Report and Written Opinion for Application No. PCT/US2004/025458 mailed Nov. 30, 2004.
International Search Report and Written Opinion for Application No. PCT/US2010/030131.
International Search Report dated Oct. 1, 2003 re PCT Application No. PCT/US2003/14868.
International Search Report dated Jan. 30, 2009 re PCT/US2008/079650.
International Search Report in International application No. PCT/US00/40701, mailed Jan. 25, 2001, 3 pp.
International Search Report in International application No. PCT/US02/25555, mailed Mar. 19, 2003, 4 pp.
International Search Report of Jul. 7, 2003, Application No. PCT/US03/05968.
Japanese Office Action of Feb. 3, 2009, Application No. 2003-577779.
Oasis Dry Suction Chest Drains; Instructions for Use; Atrium Medical Corporation, Hudson New Hampshire, on Mar. 27, 2002,pp. 1-4.
PCT International Search Report from corresponding PCT Application No. PCT/US2007/007923, dated May 20, 2008 in 2 pages.
PCT Preliminary and Written Report from corresponding PCT Application No. PCT/US2007/007923, dated Sep. 30, 2008 in 7 pages.
PCT Search Report and Written Opinion from corresponding PCT Application No. PCT/US2004/007721 dated Mar. 12, 2004.
Tube Thorascostomy; from webmaster@merck.com/pubs/mmanual; from Website Mar. 21, 2003, pp. 1,2.
Understanding Chest Drainage; from webmaster@nursingceu.com; from website on Mar. 21, 2002; pp. 1-15.

Amendment mailed Mar. 3, 2004 in response to Office Action dated Oct. 3, 2003 in the related co-pending U.S. Appl. No. 09/951,105.
US Office Action of Feb. 8, 2006, U.S. Appl. No. 10/103,487, filed Mar. 3, 2002.
US Office Action mailed Oct. 3, 2003 from related copending U.S. Appl. No. 09/951,105.
US Office Action of Jun. 14, 2005, U.S. Appl. No. 10/103,487, filed Mar. 3, 2002.
US Office Action of Mar. 22, 2007, U.S. Appl. No. 10/103,487, filed Mar. 3, 2002.
US Office Action of May 19, 2006, U.S. Appl. No. 10/103,487, filed Mar. 3, 2002.
US Office Action of Oct. 20, 2004, U.S. Appl. No. 10/103,487, filed Mar. 3, 2002.
US Office Action of Sep. 12, 2006, U.S. Appl. No. 10/103,487, filed Mar. 3, 2002.
US Office Action of Dec. 10, 2010, U.S. Appl. No. 11/880,090, filed Jul. 19, 2007.

* cited by examiner

BRONCHOSCOPIC LUNG VOLUME REDUCTION METHOD

CROSS-REFERENCE TO RELATED APPLICATIONS

The present application is a continuation application of U.S. application Ser. No. 11/417,944, filed on May 3, 2006 now abandoned, which is a continuation of U.S. application Ser. No. 10/409,785, filed Apr. 8, 2003, now U.S. Pat. No. 7,100,616. The foregoing application and patent are hereby incorporated by reference in their entirety.

BACKGROUND OF THE INVENTION

1. Field of the Invention

The invention relates in general to the field of pulmonary disease treatments, and specifically to a bronchoscopic method of performing lung volume reduction surgery using an obstruction or one-way valve.

2. Description of the Related Art

The lungs deliver oxygen to the body by directing air through numerous air passageways that lead from the trachea to respiratory bronchiole to small sacs called alveoli. These alveoli are generally grouped together in a tightly packed configuration called an alveolar sac, and surround both alveolar ducts and respiratory bronchiole throughout the lung. The alveoli are small, polyhedral recesses composed of a fibrillated connective tissue and surrounded by a few involuntary muscular and elastic fibers. These alveoli inflate and deflate with the respiration of air. Oxygen and carbon dioxide are exchanged through the ultra-thin walls between alveoli and capillary sized blood vessels.

During inhalation, as the diaphragm contracts and the ribs are raised, a vacuum is created in the chest, and air is drawn into the lungs. As the diaphragm relaxes, normal lungs act like a stretched balloon and rebound to the normal relaxed state, forcing air out of the lungs. The elasticity of the lungs is maintained by the supportive structure of the alveoli. This network of connective tissue provides strength to the airway walls, as well as elasticity to the lungs, both of which contribute to the lung's ability to function effectively.

Patients with chronic obstructive pulmonary disease or emphysema have reduced lung function and efficiency, typically due to the breakdown of lung tissue. Lung tissue and alveoli are destroyed, reducing the supportive structure of the airways. This reduction in strength of the airway walls allows the walls to become "floppy," thereby losing their ability to remain open during exhalation. In the lungs of an emphysema patient, the walls between adjacent alveoli within the alveolar sac deteriorate. This wall deterioration is accelerated by a chronic inflammatory state with the production of mucus in the lungs. Although the break down of the walls of the alveoli in the lungs occurs over time even in a healthy patient, this deterioration has greatly accelerated in people with emphysema so multiple large spaces with few connecting walls replace the much smaller and more dense alveoli in healthy lung tissue. When many of the walls of the alveoli have deteriorated, the lung has larger open spaces (bullae or air cavity) and a larger overall volume, but has less wall tissue to conduct gas exchange.

In this diseased state, the patient suffers from the inability to get the air out of their lungs due to the loss of elasticity of the lungs as well as the collapse of the airways during exhalation. Heavily diseased areas of the lung become hyperinflated. Within the confines of the chest cavity, this hyperinflation restricts the in-flow of fresh air and the proper function of healthier tissue, resulting in significant breathlessness. Thus, the emphysematous patient attempts to take in a greater volume of air to achieve the same amount of gas exchange. With, severe emphysema, when patients take in as much air as their chest cavity can accommodate, they still have insufficient gas exchange because their chest is full of non-functional air filling large cavities in the lungs. Emphysema patients will often look barrel-chested and their shoulders will elevate as they strain to make room for their hyperinflated lungs to work.

A wide variety of drugs are available for treating the symptoms of chronic obstructive pulmonary disease, but none are curative. Chronic bronchitis and emphysema are typically treated with antibiotics and bronchodilators. A large number of patients are not responsive to these medications. In selected severe emphysema cases, lung volume reduction surgery (LVRS) is performed to improve lung efficiency and to allow the patient to improve breathing function and quality of life. In lung volume reduction surgery, the most diseased portion of an emphysematous lung having a large amount of alveolar wall deterioration is surgically removed. LVRS is performed by surgically entering the chest cavity then stapling off and resecting the diseased portion(s) of the lung(s). This allows the remaining healthier lung tissue to inflate more fully and take greater advantage of the chest mechanics to inhale and exhale. Because there is more air and more gas exchange in the healthier portion of the lung, lung efficiency is improved and patients feel better.

Traditional lung volume reduction surgery is an invasive procedure requiring surgically entering the chest cavity and removal of lung tissue. This surgery has substantial risks of serious post-operative complications, such as pneumonia, and requires an extended convalescence. There have been more recent attempts to achieve lung volume reduction through minimally-invasive procedures. For example, U.S. Pat. Nos. 6,293,951 and 6,258,100 to Alferness et al. describe methods of collapsing a lung portion by obstructing an airway. U.S. Pat. No. 6,488,673 to Laufer et al. describes a method of increasing gas exchange of a lung by causing tissue damage within a diseased airway in order to cause the airway to remain open. U.S. Patent Application Publication No. 2001/0051799 to Ingenito teaches another method of non-surgical lung volume reduction that involves injecting a polymerizable sealant into a diseased lung section. Notwithstanding the benefits of the above methods, minimally invasive lung volume reduction may be performed utilizing other advantageous methods.

SUMMARY

The present invention comprises methods of performing lung volume reduction to address a diseased lung section. One method comprises the steps of deflating a target lung section minimally invasively, causing inflammation of the walls of the target lung section, and placing an occlusion device within an airway leading to the target lung section to temporarily prevent re-inflation of the target section. By causing inflammation of the target lung walls, that portion of the lung will seal at a smaller volume. The method comprises guiding a catheter to the target lung section via the patient's trachea and bronchi, exposing the cavity within the target lung section to the ambient environment to deflate the air cavity, and injecting an inflammation-causing substance, preferably the patient's blood or analogous compatible fluid, onto walls of the air cavity. The volume of the cavity of the target lung section will be permanently maintained in a reduced state because the walls of the cavity come into substantial contact with one another, eventually substantially adhering to one another. Temporary re-inflation is prevented during the adhesion process by placing an occlusion device in an airway upstream of the portion of the lung to be treated, as close to the cavity as feasible, although general proximity is not critical. The catheter is then removed while temporarily leaving the occlusion device in the airway.

In one application of the present method, the distal end of a bronchoscope is used to guide the catheter to a diseased lung section, where an inflammation-causing substance is injected into the diseased lung section. In one variation, the present method comprises using the distal end of a bronchoscope to guide a multilumen catheter to a position adjacent the target region, inserting a puncturing tip through a section of diseased lung tissue and into the target region, and equilibrating the target region with atmospheric air. The target region air is equilibrated through a lumen extending from a distal opening of the lumen to the atmosphere. With the target region at atmospheric pressure, one or more occlusion devices may then be deployed in airways leading into the target region, thereby isolating the target region from inspiratory air flow. In one application, the obstruction is a one-way valve, such as those described in the '951 and '100 Alferness patents, or those described in pending U.S. patent application Ser. No. 09/951,105 to Alferness et al. filed on Sep. 11, 2001, Ser. No. 10/104,487 to Alferness et al. filed on Mar. 30, 2002, and Ser. No. 10/124,790 to DeVore filed on Apr. 16, 2002. The entire disclosures of the above patents and applications are incorporated herein by reference and made part of the present disclosure. The advantage of an obstruction device is reduced risk of reinflation during the adhering process, resulting in more effective lung volume reduction. Another advantage, among others, is precluding migration of the injected substance to non-targeted regions of the lung.

DETAILED DESCRIPTION

Figure 1:
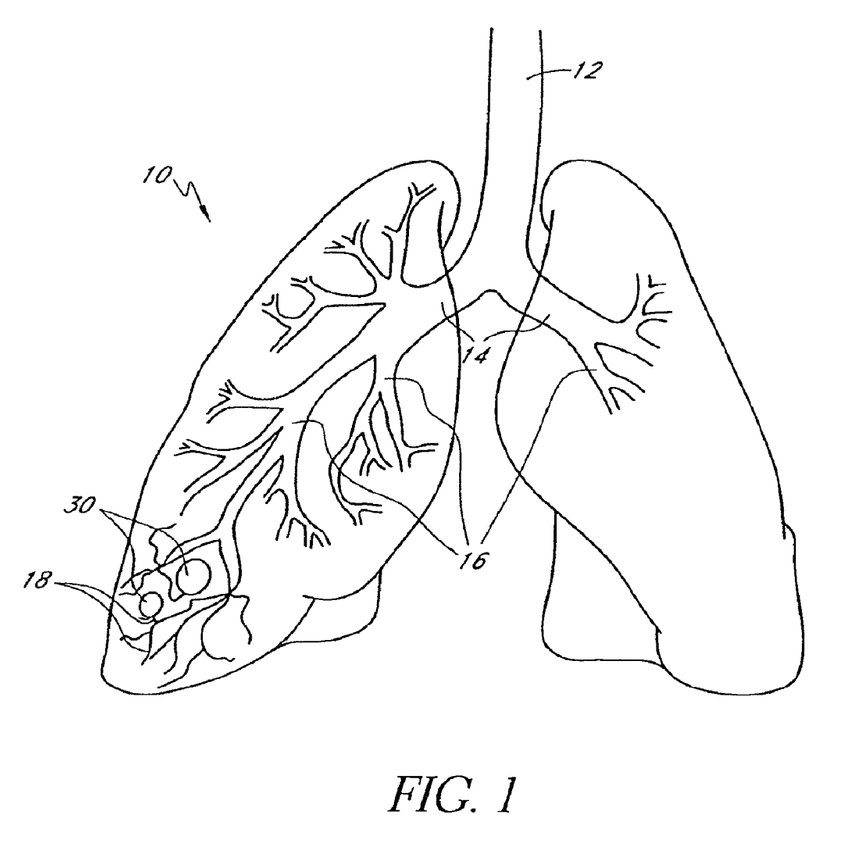
FIG. 1 is a schematic view of a pair of lungs.
Figure 2:
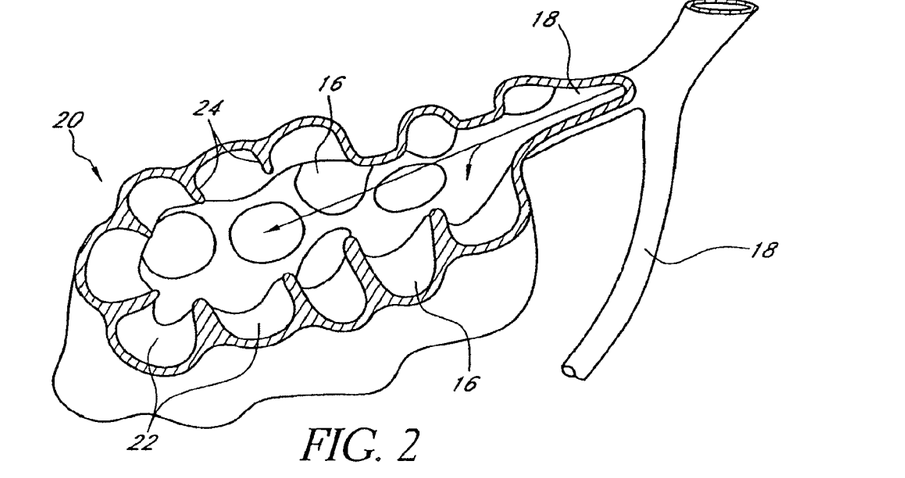
FIG. 2 is a schematic sectional view of a portion of healthy lung with intact alveolar sacs.

The methods described herein involve minimally invasive procedures for reducing the volume of a diseased target region of a patient's lung. Referring to FIGS. 1 and 2, airflow in a lung 10 to be treated generally follows a path from the trachea 12, through the main branch bronchial tubes 14, then through the sub-bronchial tubes 16 to the numerous tiny bronchioles 18. The bronchioles 18 lead to alveolar sacs 20 which include multiple alveoli 22 separated by alveolar walls 24 for the exchange of oxygen and carbon dioxide. In lungs suffering from emphysema, the alveolar walls 24 are deteriorated, thus leaving a number of large open spaces or cavities 30. Often, the largest of such cavities 30 will be chosen as a target region 32 for volume reduction first, although the specific regions to be reduced will be chosen by a clinician based on a number of factors. A target region 32 of diseased lung to be reduced in volume will generally include at least one enlarged target cavity 34.

The cavities 30 (otherwise called bullae) are typically larger than 10 mm in diameter, and in some cases can be much larger (up to 6 cm or more in diameter). The airways leading to the bullae 30 are often not obvious or easily located, and can often be smaller than 1 mm in diameter. Additionally, there may often be multiple small airways leading to a single cavity 30.

Figure 3:
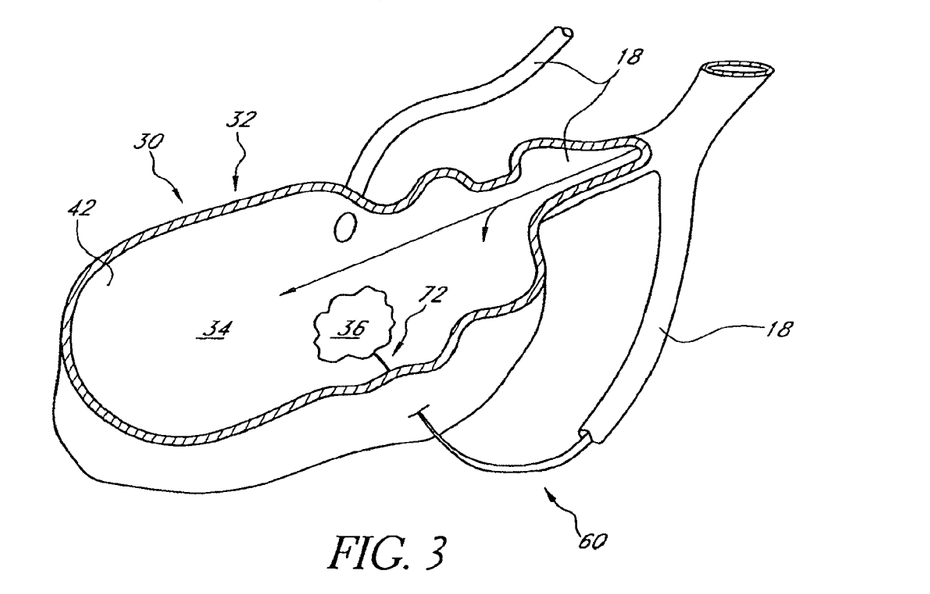
FIG. 3 is a schematic sectional view of a portion of an emphysematous lung in which the alveolar walls have deteriorated leaving an air cavity or bullae.
Figure 4:
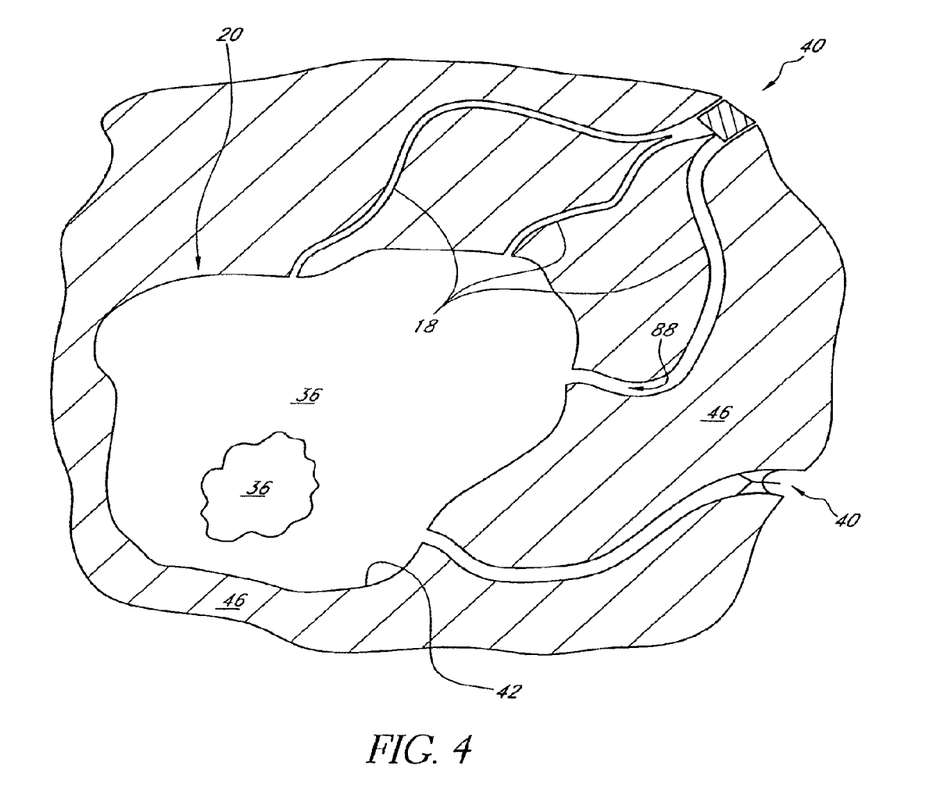
FIG. 4 is a schematic view of a lung tissue cavity to be reduced in volume in accordance with aspects of the present invention.

With reference to FIGS. 3 and 4, the methods described herein generally comprise the steps of gaining access to a hyper-inflated cavity 34 of a target region 32 by introducing a means for reducing the volume of the target region, equilibrating air within the target region with atmospheric pressure, injecting an inflammation-causing substance 36 into a cavity 34 of the target region 32, preventing re-inflation of the target region 32 by temporarily deploying one or more occlusion device 40 for a sufficient time to allow the tissue surrounding the cavity 34 to sclerose and adhere together, and finally removing the occlusion device 40 at some later time. By removing the air from within the target region first, the walls 42 of the cavity 34 forming the target region 32 can be brought into substantial contact with one another. Inflammation occurring in the lung tissue 46 of the inner walls 42 of the cavity 34 will cause the cavity walls 42 to begin adhering together. After a period of time, the walls 42 of the target section 32 will permanently adhere. During this time, the target region 32 is preferably isolated from inspiratory air flow by one or more occlusion devices in order to prevent re-inflation of the target region.

The occlusion device is configured to substantially preclude inspiration downstream of said device, and in one application comprises a one-way valve that allows the flow of fluid, whether gas or liquid, in one direction and substantially precludes fluid flow in an opposite direction. Suitable occlusion device deployment structures are described, for example, in co-pending U.S. patent application Ser. No. 10/052,875 to Rimbaugh et al. filed on Oct. 10, 2001, the entire disclosures of which is incorporated herein by reference. By way of brief summary, one example of the one-way valve may be configured in the shape of an umbrella comprising a frame that is configured to exert radial forces against the wall of the airway passage. Such an arrangement would preclude substantial inspiration to the lung downstream of the placement of the device, but permit some limited fluid flow upstream, such as experienced with mucocilliary transport. In another configuration, the one-way valve may comprise a stent-supported valve.

With reference to FIGS. 3-6, a means for reducing the volume of a target region 32 of a lung can include one of a number of known or newly developed devices. In one embodiment, means 44 for reducing the volume of a target region 32 comprises a conventional bronchoscope 50 having a visualizing tip 52 and at least one lumen 54. A wide variety of bronchoscopes are commercially available, many of which will be suitable for carrying out portions of the volume reduction procedure described herein. Typical bronchoscopes have an outer diameter of about 5 mm, although larger or smaller bronchoscopes could also be used. Alternatively, any number of other devices could be used in place of a conventional bronchoscope. Specifically, any device that allows a clinician to gain visual and functional access to the interior of a patient's lungs could be used. Such alternative devices could include laparoscopes, endoscopes, or any other elongate, flexible scope with at least one working lumen and/or one or more tools mounted on a distal end thereof. In addition to the visualizing capabilities of any bronchoscope (or other scope) that may be used, a clinician may decide to use X-ray, ultrasonic, radiographic, or other visualization systems to provide supplemental visualization during the volume-reduction procedure.

Figure 6:
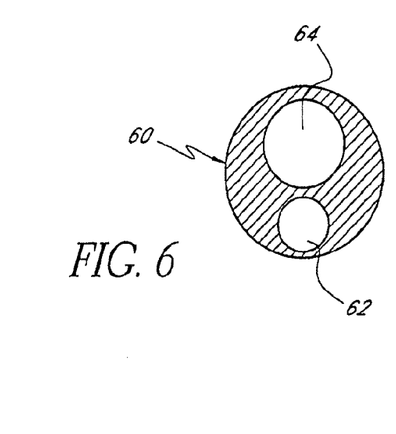
FIG. 6 is a cross-sectional view of a dual-lumen catheter which can be used to reduce a volume of a target lung section.

Suitable means for reducing the volume of a target region often further includes one or more elongate, flexible catheters 60 with one or more lumens extending therethrough. Suitable catheters preferably have as small an outside diameter as possible, while maintaining sufficient column strength for the catheter to be advanced through a patient's airways without buckling or kinking. For example, in some embodiments catheters may be provided with an outer diameter of about 2 mm, although larger and smaller catheters can also be used. At least one lumen of at least one catheter is preferably adapted to allow airflow therethrough. Additionally, at least one lumen of at least one catheter is typically adapted to transmit a liquid therethrough. For example, FIG. 6, illustrates a cross-section of a single catheter 60 with a first lumen 62 for transmitting air therethrough, and a second lumen 64 for transmitting a liquid therethrough. The liquid 64 and airflow 62 lumens can be any suitable size as desired. Alternatively the airflow and liquid-flow lumens could be provided in separate, single-lumen catheters. As will be clear to the skilled artisan in view of the present disclosure, a single lumen can alternatively be used for transmission of both air and liquid if so desired. Alternatively still, a working lumen 54 of a bronchoscope 50 can comprise an airflow and/or a liquid flow lumen.

If desired, the airflow lumen 62 can include a valve for limiting airflow in one or both directions through the airflow lumen 62. The airflow lumen 62 can also optionally include a pressure gauge or sensor for indicating an air pressure level or a change in air pressure at the distal end of the catheter 60. If desired, a proximal end of the airflow lumen can also include a fitting for receiving a pump, such as a vacuum pump, to force airflow in one or both directions. The liquid-carrying lumen 64 can include a syringe, plunger, or other device for injecting a liquid substance through the liquid-carrying lumen 64.

Figure 5:
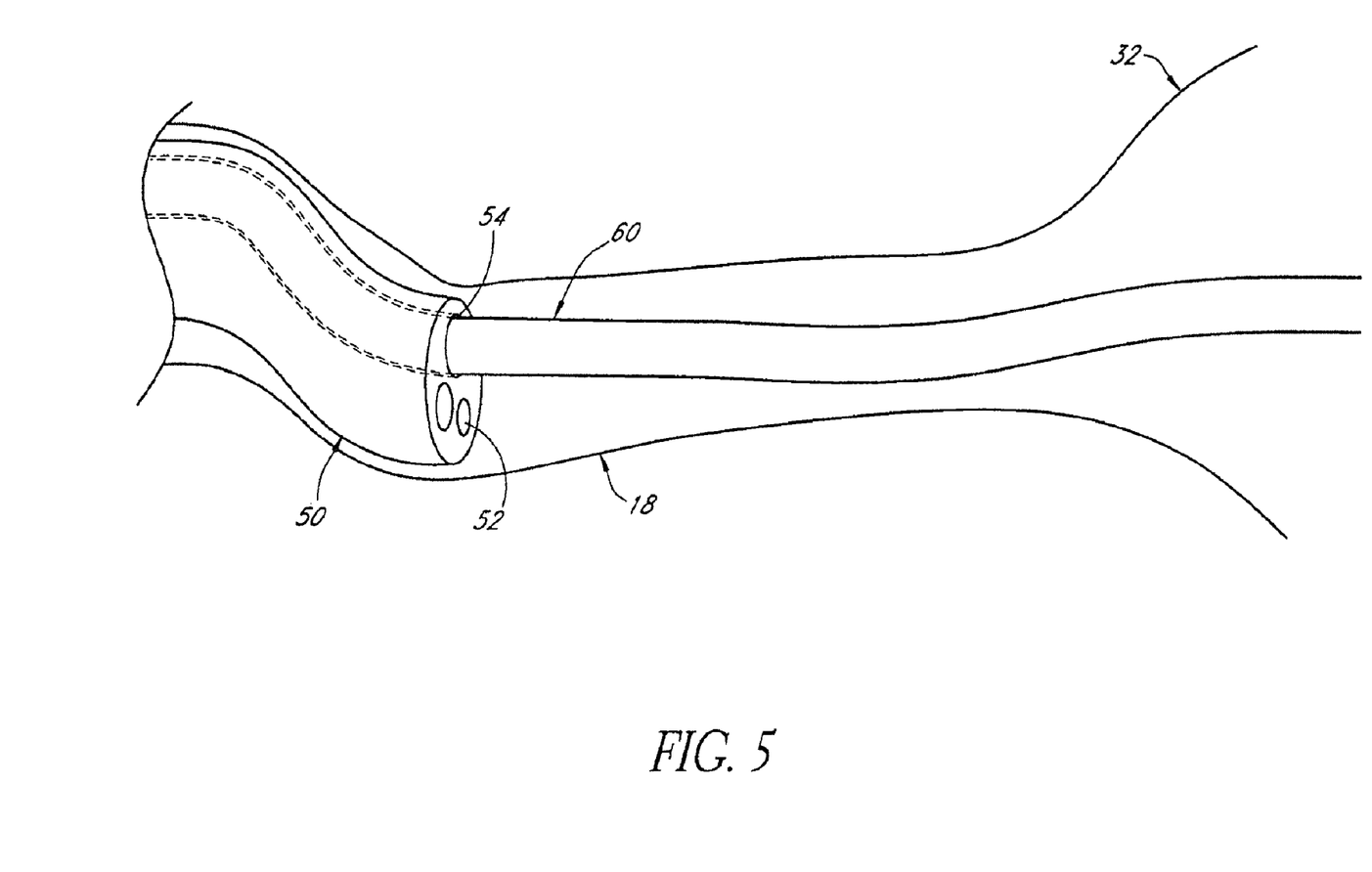
FIG. 5 is a cross-sectional view of an airway with a bronchoscope positioned adjacent a target lung section to be reduced in volume, and a catheter extending through a working lumen of the bronchoscope.
Figure 5A:
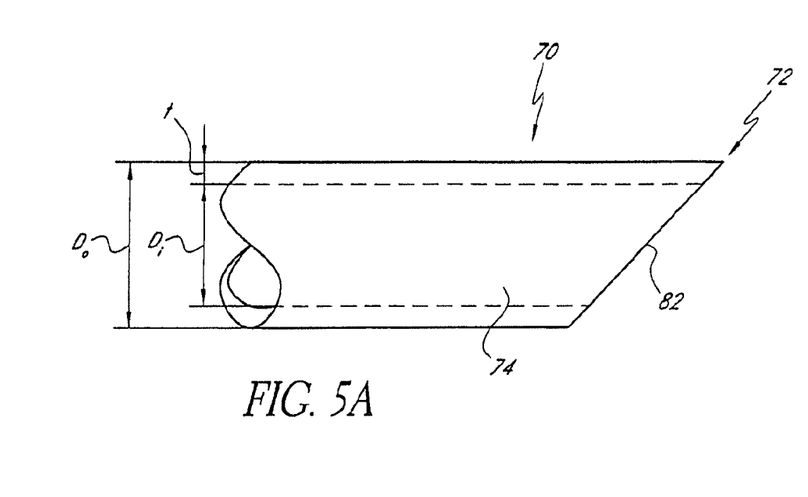
FIG. 5a is a detail view of one embodiment of a distal tip for use with the catheter of FIG. 4.
Figure 5B:
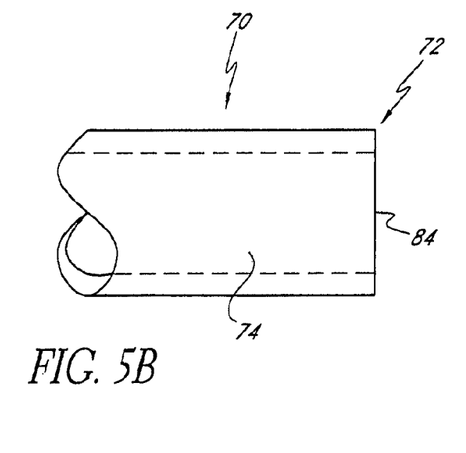
FIG. 5b is detail view of another embodiment of a distal tip for use with the catheter of FIG. 4.

A distal end 70 of at least one catheter 60 can also include a puncturing tip 72 as shown in FIGS. 5a and 5b. In many cases, a particular diseased target region 32 may not be easily reachable with a bronchoscope translumenally in part due to the difficulty in navigating the tortuous pathways between the trachea 12 and the target alveoli 16. Additionally, the walls of a bronchiole 18 leading into a hyper-inflated diseased lung portion 30 can become flaccid and collapsed, precluding effective passage of the bronchoscope or catheter therethrough. Thus, in many cases it may be easier and more effective to navigate the distal end of a bronchoscope to a section of the lung that is adjacent to the target region 32 and then puncture through a section of lung tissue 46 in order to gain access to the hyper-inflated target region 32. In other cases, it may be necessary to puncture through the collapsed walls of an airway 18 leading into a target region 32.

Such puncturing can be accomplished with a device such as a needle or tapered tip mounted on a distal end of a bronchoscope. Alternatively, a suitable tool can be mounted on a distal end of a catheter that can be passed through a lumen 54 of a bronchoscope 50 to extend beyond the distal end of the scope in order to be used to puncture the tissue as desired. A catheter 60 with at least one lumen configured to carry a liquid or a gas therethrough can be fitted with a substantially rigid puncturing tip 72. Puncturing tips 72 can include a variety of shapes, and typically have a hollow central lumen 74 therethrough. The puncturing tip generally has as small an outer dimension '$D_o$' as possible in order to minimize the size of a hole created in the lung tissue, an inner dimension '$D_i$' that is large enough to transmit an inflammation-causing substance therethrough, while maintaining a wall thickness 't' sufficient to provide the puncturing tip 72 with sufficient columnal strength for the tip to puncture a desired segment of lung tissue. For example, in some embodiments, a puncturing tip with a circular cross-section can have an inner diameter '$D_i$' of between about 0.5 mm and about 2 mm, often between about 0.75 mm and about 1.5 mm, and in one embodiment, the puncturing tip has an inner diameter '$D_i$' of about 1 mm.

In one embodiment, the puncturing tip 72 can be a stainless steel needle affixed to the distal end of a catheter 60. If desired, the needle can have either a sharp tapered tip 82 or a substantially blunt tip 84 as shown in FIGS. 5a and 5b respectively. Other shapes for atraumatic tips exist and are known to those skilled in the art, which could be used to allow a catheter and/or bronchoscope to be atraumatically navigated through a patient's bronchial passageways in the procedure described herein. A puncturing tip or an atraumatic tip can also be provided with a plurality of holes or ports for the injection or uptake of fluids or gasses into or out of a cavity 30.

Alternatively still, the puncturing tip 72 can be made of any suitable material, such as other metals or a molded or extruded plastic, provided that the puncturing tip has sufficient columnal strength to allow the tip to puncture the lung tissue to a desired depth. Thus, a section of rigid material having any hollow tubular cross-sectional shape can be used to puncture into a target region. Thus, a catheter 60 with a puncturing tip 72 can then be introduced through lumen 54 of means 44 for reducing the volume of the target region 32, and the tip 72 can be punctured through the lung tissue into the target region 32, as shown in FIG. 3. Where the step of puncturing the target wall is desired or necessary, the step of deploying the obstruction device prior to the introduction of the inflammation triggering substance may be advantageous.

Occlusion devices 40 can generally be deployed using any suitably configured catheter. For example, an occlusion device deployment catheter can include a distal cavity for retaining at least one occlusion device to be deployed in a patient's airway and a means for deploying the occlusion device. The means for deploying the occlusion device can include any suitable structure such as a push wire that is extendable through the length of the catheter and can be operated by a clinician to push the occlusion device out of the catheter. Alternatively, the means for deploying the occlusion device could include a retractable sheath that can be retracted relative to the occlusion device, thereby releasing the occlusion device.

The occlusion device can be one of many devices recognized as being suitable for occluding the flow of air in an anatomical lumen. For example, the '951 patent to Alferness et al. shows and describes a number of devices for unidirectionally and bidirectionally occluding airflow through an airway. Additionally, co-pending U.S. patent application Ser. No. 10/143,353 filed on May 9, 2002 shows and describes embodiments of a one-way valve that can also be used to prevent re-inflation of the target region while advantageously allowing mucous and other fluids to be moved proximally past the valve. PCT publication WO 98/48706 to Sabanathan shows and describes a number of plug-type occlusion devices that will occlude both inspiratory and expiratory air flow. The above-mentioned patents and applications are incorporated herein by reference and made part of the present specification.

Suitable occlusion devices can be provided in any size or configuration as desired. For example, in some embodiments, one-way valve occlusion devices having expanded outer diameters of between about 3 mm and about 8 mm can be used. Alternatively, valves having outer expanded diameters as small as 1 mm or less could be used.

The occlusion devices for use with the present inventive method can generally be adapted to be removed from a patient's airway after the volume of the target region has been permanently reduced. A means for removing the occlusion device 40 can include an elongate, flexible removal catheter with an occlusion device receiving space, and a means for gripping the occlusion device. The occlusion device receiving space can simply be a lumen of sufficient diameter to allow an occlusion device to be drawn into the space. If desired, the occlusion device receiving space can be sized to receive a plurality of occlusion devices, thereby eliminating the need to remove and re-introduce the removal catheter when removing multiple occlusion devices 40. A means for gripping an occlusion device 40 can include any suitable trans-luminal gripping tool, such as forceps, etc. Alternatively, a means for removing an occlusion device could simply include a bronchoscope. Accordingly, the occlusion device could be drawn into a lumen of the scope, thus allowing the occlusion device and the bronchoscope to be simultaneously removed. In an alternative embodiment, portions of the occlusion devices 40 can be made from a substantially bioabsorbable polymer which will be substantially dissolved and absorbed by a patient's body fluids and tissue, thereby eliminating the need for bronchoscopic removal of the occlusion device(s).

The methods of the present invention can be carried out with the above devices or any other tools or devices recognized as suitable by the skilled artisan. Once accessed, the hyper-inflated target lung portion 32 can be deflated by opening an airflow lumen 62 to bring the distal end of the lumen 62 (including any puncturing tip) in fluid communication with the ambient air at atmospheric pressure, thereby allowing the air in the target lung section 32 to equilibrate with atmospheric air pressure. In one preferred application, the target region 32 is maintained at atmospheric pressure throughout the procedure described herein. In some cases it may be desirable to further extract air from the target region 32 by applying a net negative pressure to an airflow lumen 62. In either case, the walls of the opposing side of the cavities within the target lung regions will be brought sufficiently close to permit adhesion. Where no net negative pressure is applied to the cavity or cavities, the residual air will eventually be absorbed or be drawn out through expiration, permitting the opposing walls to move closer and accelerating the adhesion process.

With reference to FIGS. 3 and 4, it has been observed that blood applied to a section of lung tissue will cause the lung tissue to become inflamed, thereby causing the tissue to become substantially adherent. The opposing wall sections of deflated lung tissue will eventually grow together, over a relatively short period of time, to create a substantially permanent and natural bond. Thus, in one preferred application, a substance 36 such as whole blood or a constituent or derivative of blood can be injected into the target region 32 to cause inflammation of the walls 42 surrounding a cavity 34 of a target region 32. Blood components such as plasma, serum, fibrin, etc can be used individually or in various combinations as needed in order to provide the desired result. Blood or blood-derived substances to be injected into the target region 32 can be obtained from the patient before the procedure is carried out. By using autologous blood or blood constituents, the risk of rejection by the patient's body and the risk of contamination with a blood-transmitted infection can be substantially reduced, or even eliminated. In some cases, it may be desirable to mix the blood or blood constituent with an anti-coagulant such as Heparin, or a diluting physiological solution such as saline. Alternatively, a pure sample of whole blood or a blood constituent that is substantially free from foreign substances could be used if desired. Alternatively still, the same effect may be achievable with other body fluids (autologous or from a compatible donor). The particular effectiveness of other non-blood-derived body fluids as inflammation-causing substances can be determined by routine experimentation in view of the present disclosure.

Alternatively still, other organic and non-organic, inflammation-triggering, substances, gaseous or liquid, heated or cooled, may be used to cause inflammation of the lung tissue surrounding an enlarged cavity. For example, U.S. Patent Application Publication No. 2001/0051799 to Ingenito (incorporated in its entirety herein by reference, shows and describes a number of fibrosis-causing substances. Hot saline solution or very cold liquids or gasses may also be used.

The volume of an inflammation-causing substance to be injected into the target region cavity 34 will depend upon a number of factors, such as the type of substance being used (e.g. whether the substance is blood, another liquid or a gas), the approximate volume or inner wall surface area of the target region cavity, and other variables, such as the viscosity of the liquid substance used. In the case of liquid inflammation-causing substances, a sufficient volume of liquid to coat a substantial portion of the entire surface of the tissue 46 surrounding the target region cavity 34 should be used. It is generally preferred, that the substance 36 injected into a target region 32 be kept from causing inflammation of any adjacent healthy lung tissue. Deployment of the obstruction device upstream of the target region is beneficial in that regard.

If blood or a blood constituent is to be used as the inflammation-causing substance, a volume of blood that is between about 1 and about 100 percent of the volume of the target region cavity 34 can be used, where the volume of blood is preferably between about 5 and about 15 percent of the volume of the target region cavity 34. In one preferred application of the present invention, the volume of blood is about 10 percent of the volume of the target region cavity 34. For example, in order to reduce the volume of a cavity 30 with an interior diameter of about 6 cm (which can have an interior volume of about 113 cc, assuming a sphere), a volume of about 10 to about 20 cc of a liquid substance such as blood could be injected to coat the interior walls of the cavity. If necessary, any excess liquid can be removed from the target region by drawing a vacuum through a catheter lumen, or any other suitable method. In order to ensure a greater coating of the walls of the target region cavity 34 with the substance, the patient may need to roll over a few times, or make other similar movements.

In some cases, the walls 42 of the target region 32 can take a substantial length of time to permanently grow together. Depending on factors such as the size of the target region cavity 34, the inflammation-causing substance used, etc, complete adhesion of the walls of the target region can take anywhere from a few days to about a month or more. During this time, it is important that the target region be substantially protected against re-inflation. In many cases of advanced emphysema, a particular target region cavity 34 in the lungs can have a plurality of airways 18 (e.g. bronchioles) leading into the cavity 34. If all of these airways remain open to air flow after injection of the substance 36, the cavity 34 can become re-inflated, thereby potentially frustrating the objective of the lung volume-reduction procedure. Thus, either before or after injecting the inflammation-causing substance into the target region cavity 34, the airways 18 leading into the cavity 34 can be at least partially occluded by deploying one or more occlusion devices 40 into the lumens of the airways 18. It may not be necessary, however, to occlude every individual airway leading into the cavity, as this may prove to be prohibitively difficult in some cases.

In order to successfully prevent re-inflation, an occlusion device 40 may be deployed in an airway 18 substantially upstream from the target region 32. Occasionally it may be necessary to occlude an airway that feeds healthy lung tissue in addition to the target region 32. It is preferred that the placement of the occlusion devices 40 will occlude a minimum of airways extending through healthy lung tissue.

Once the occlusion device deployment and substance-injection procedures have been completed, the bronchoscope and any other trans-bronchial tools can be withdrawn from the patient, thus leaving the injected substance and occlusion devices in place relative to the target region. The inventive procedures allows the patient to be ambulatory while the walls 42 of the target region substantially completely sclerose. Depending upon the patient and the particular substance injected, the time required to sclerose will vary. The occlusion device(s) can be removed after a clinician has verified that the volume of the target region has been substantially permanently reduced. Verification of volume reduction can be accomplished by evaluation of a patient's symptoms, testing a patient's breathing function (e.g. breathing effort, etc), and/or by imaging of a patient's lungs such as by x-ray or MRI scans.

Once the volume of the target region has been permanently reduced, a suitable means for removing an occlusion device 40 can be introduced through the patient's airways to a position adjacent an occlusion device 40. Once in position, the means for removing an occlusion device can be operated in an appropriate manner to remove one or all of the occlusion devices 40. Multiple occlusion devices 40 can be removed in any suitable sequence, and if desired, without removing the bronchoscope 50 with each occlusion device 40. Alternatively, it is contemplated that one embodiment of an occlusion device comprises a bio-absorbable polymer, which can be left in place and allowed to deteriorate, thereby "removing" the occlusion device without introducing a bronchoscope or a removal catheter.

In an alternative application of the present method, the substance-injection step can be omitted, where one or more occlusion devices are left in place for a sufficiently long period of time that the walls surrounding the cavity substantially permanently adhere naturally.

Although certain embodiments and examples have been described herein, it will be understood by those skilled in the art that many aspects of the methods and devices shown and described in the present disclosure may be differently combined and/or modified to form still further embodiments. Additionally, it will be recognized that the methods described herein may be practiced using any device suitable for performing the recited steps. For example, the target region volume could be reduced by the present method using conventional open-chest surgical procedures. Such alternative embodiments and/or uses of the methods and devices described above and obvious modifications and equivalents thereof are intended to be within the scope of the present disclosure. Thus, it is intended that the scope of the present invention should not be limited by the particular embodiments described above, but should be determined only by a fair reading of the claims that follow.

What is claimed is:

1. A method of delivering a gas to a lung region comprising:
   steering a bronchoscope through an air passageway to position a distal end of the bronchoscope near a diseased target region, wherein the diseased target region comprises a hyper-inflated cavity in a lung;
   inserting a catheter through a lumen of the bronchoscope to position a distal end of the catheter near or in the diseased target region;
   at least partially deflating the diseased target region by exposing the diseased target region to an ambient environment through the catheter to equilibrate the diseased target region with the ambient environment such that the diseased target region is at ambient pressure;
   placing, using the catheter, an occlusion device within the air passageway leading to the diseased target region after equilibrating the diseased target region with the ambient environment; and
   delivering, using the catheter, the gas to the diseased target region, wherein the gas is an inflammation-triggering gas for treating the diseased target region wherein the diseased target region is maintained substantially at ambient pressure during the placing and the delivering.

2. The method of claim 1, wherein the gas delivered to the target region is a vapor.

3. The method of claim 1, wherein the gas delivered to the target region is a heated gas.

4. The method of claim 1, wherein the diseased target region is an emphysematous lung section.

5. The method of claim 1, wherein the gas is configured to precipitate adhesion of walls of the diseased target region.

6. The method of claim 1, wherein the gas is configured to reduce hyper-inflation of the diseased target region.

7. The method of claim 1, wherein placing the occlusion device comprises placing a plurality of occlusion devices.

8. The method of claim 1, wherein the occlusion device is decoupled from the catheter after placing the occlusion device within the air passageway leading to the diseased target region.

9. The method of claim 1, wherein delivering the gas to the diseased target region comprises delivering the gas through the catheter.

10. The method of claim 1, further comprising drawing a vacuum through the catheter.

11. The method of claim 1, further comprising removing the occlusion device after a period of time from the delivering of the gas.

12. The method of claim 11, wherein the period of time allows inner walls of the diseased target region to adhere together.

13. The method of claim 1, wherein the occlusion device is a one-way valve that allows a flow of fluid in one direction and substantially precludes a fluid flow in an opposite direction.

14. The method of claim 13, wherein the one-way valve is a stent-supported valve.

15. The method of claim 1, wherein the occlusion device is a plug-type occlusion device.

16. The method of claim 1, wherein the occlusion device is configured to preclude migration of the gas to non-targeted regions.

17. The method of claim 1, wherein the exposing the disease target region to ambient environment to equilibrate the diseased target region with the ambient environment is performed without the use of pulsatile suction.

18. The method of claim 1, wherein the occlusion device comprises bioabsorbable polymer.

19. The method of claim 1, wherein the catheter comprises a pressure gauge or sensor for indicating an air pressure level at the distal end of the catheter.

* * * * *